US012661244B2

(12) United States Patent
Pusch

(10) Patent No.: US 12,661,244 B2
(45) Date of Patent: Jun. 23, 2026

(54) ORTHOPEDIC JOINT DEVICE

(71) Applicant: Ottobock SE & Co. KGAA, Duderstadt (DE)

(72) Inventor: Martin Pusch, Duderstadt (DE)

(73) Assignee: OTTOBOCK SE & CO KGAA, Duderstadt (DE)

( * ) Notice: Subject to any disclaimer, the term of this patent is extended or adjusted under 35 U.S.C. 154(b) by 863 days.

(21) Appl. No.: 17/416,409

(22) PCT Filed: Dec. 10, 2019

(86) PCT No.: PCT/EP2019/084499
§ 371 (c)(1),
(2) Date: Jun. 18, 2021

(87) PCT Pub. No.: WO2020/126697
PCT Pub. Date: Jun. 25, 2020

(65) Prior Publication Data
US 2022/0117761 A1      Apr. 21, 2022

(30) Foreign Application Priority Data

Dec. 20, 2018      (DE) .......................... 102018133063.4

(51) Int. Cl.
*A61F 2/74*          (2006.01)
*A61F 2/50*          (2006.01)
(Continued)

(52) U.S. Cl.
CPC .............. *A61F 2/748* (2021.08); *A61F 2/582* (2013.01); *A61F 2/64* (2013.01);
(Continued)

(58) Field of Classification Search
CPC .. A61F 2/748; A61F 2/582; A61F 2/64; A61F 2002/5035; A61F 2002/5038; A61F 2002/6818; A61F 2/74
See application file for complete search history.

(56) References Cited

U.S. PATENT DOCUMENTS 5,888,212 A       3/1999  Petrofsky
2015/0164660 A1   6/2015  Will
(Continued)

FOREIGN PATENT DOCUMENTS

DE       202006007641 U1     8/2006
DE       102008024747 A1     12/2009
(Continued)

OTHER PUBLICATIONS

International Search Report and Written Opinion issued in PCT/EP2019/084499, dated Mar. 20, 2020, 7 pgs.

*Primary Examiner* — Bruce E Snow
(74) *Attorney, Agent, or Firm* — HOLLAND & HART LLP

(57) ABSTRACT

The invention relates to an orthopedic joint device having an upper part and a lower part which is hinged about a pivot axis to said upper part, having a flexion moment-controlled retainer device that is positioned between the upper part and the lower part, blocks a flexion and releases the flexion when a predefined flexion moment is exceeded, wherein a control element is associated with the retainer device and is coupled to a delaying element.

21 Claims, 5 Drawing Sheets

(51) Int. Cl.

| | |
|---|---|
| *A61F 2/58* | (2006.01) |
| *A61F 2/64* | (2006.01) |
| *A61F 2/68* | (2006.01) |

(52) U.S. Cl.

CPC ................. *A61F 2002/5035* (2013.01); *A61F 2002/5038* (2013.01); *A61F 2002/6818* (2013.01)

(56) References Cited

U.S. PATENT DOCUMENTS

| | | | |
|---|---|---|---|
| 2015/0182354 A1 | 7/2015 | Bonnet | |
| 2016/0038312 A1 | 2/2016 | Kampas | |
| 2017/0042703 A1 | 2/2017 | Pusch | |
| 2017/0079810 A1 | 3/2017 | Clausen | |
| 2018/0256380 A1* | 9/2018 | Pusch | ................... A61F 5/0102 |
| 2019/0307582 A1 | 10/2019 | Seyr | |

FOREIGN PATENT DOCUMENTS

| | | | |
|---|---|---|---|
| DE | 102012013141 A1 | 5/2014 | |
| DE | 102014006228 A1 | 11/2015 | |
| DE | 102015116149 A1 | 3/2017 | |
| DE | 102016118999 B4 | 4/2018 | |
| EP | 3137020 A1 | 3/2017 | |
| GB | 2367753 A | 4/2002 | |
| RU | 2054906 C1 | 2/1996 | |
| RU | 2096026 C1 | 11/1997 | |

* cited by examiner

ORTHOPEDIC JOINT DEVICE

CROSS-REFERENCE TO RELATED APPLICATIONS

This is a national phase application of International Application No. PCT/EP2019/084499, filed 10 Dec. 2019, which claims the benefit of German Patent Application No. 102018133063.4, filed 20 Dec. 2018, the disclosures of which are incorporated, in their entireties, by this reference.

TECHNICAL FIELD

The invention relates to an orthopedic joint device having an upper part and a lower part which is fastened to the upper part in an articulated manner about a pivot axis, with a flexion-moment-controlled retaining device which is arranged between the upper part and the lower part and which blocks flexion and releases the flexion when a predetermined flexion moment is exceeded.

BACKGROUND

The orthopedic joint device is configured in particular as an artificial prosthetic joint, a joint in exoskeletons or an orthotic joint, in particular as an artificial knee joint or elbow joint, that is not restricted to such embodiments, but rather can also be used in other regions. In an embodiment of an artificial knee joint, standing and possibly walking with a locked joint is possible with such an orthopedic joint device; after release in the flexion direction, the upper part can be pivoted relative to the lower part. However, it is also possible for the joint device to be used in the form of a so-called dynamic joint, which can counteract spastic contractions or can be used to treat the contractions by means of stretching exercises.

Locking joints, in particular so-called locking knee joints, are often used for relatively immobile patients in whom mobility may have been restricted, for example, as a result of diseases of the lower extremity. The restricted mobility means that there is a need here merely for knee joints which permit restriction-free sitting and provide the greatest possible level of reliability in mobility actions. For this purpose, these knee joints provide usually just two states, that is to say a locked, extended position and an unlocked position so that the knee joint can be moved freely. No provision is usually made for adaptation of the damping in a swing phase or stance phase. Such an artificial knee joint in the form of a prosthetic knee joint is described in DE 20 2006 007 641 U1. In order to unlock such a prosthetic knee joint, an unlocking mechanism has to be actuated by hand.

DE 10 2008 024 747 A1 relates to an orthopedic device having a joint which connects an upper part to a lower part in a pivotable manner. Connection means for fastening to a limb are arranged on the upper part. A locking device prevents a flexing movement of the upper part relative to the lower part, wherein the locking device can be actuated in active fashion by the user of the orthopedic device. A control device is assigned to the locking device which is connected to at least one sensor arranged on or in the orthopedic device, and therefore the locking device is automatically unlocked or locked depending on the sensor signal. The unlocking or locking can also be delayed by a timing switching element such that it takes place only shortly after the actual sensor signal.

An orthopedic joint device according to the preamble is described, for example, in DE 10 2015 116 149 A1.

A problem in this connection can be that the flexion moment which is required for deactivating the retaining device is set to such a high level that users of the orthopedic joint device may not be able to apply such a moment. A reduction in the release moment may possibly not be an option for safety considerations since flexion during walking may not be desired.

SUMMARY

It is therefore the object of the present invention to provide an orthopedic joint device which, while being equally reliable, provides a broad level of practicality even for patients who are capable of applying only a small flexion moment.

According to the invention, this object is achieved by an orthopedic joint device having the features of the main claim and by a damper device for use in an orthopedic joint device. Advantageous embodiments and developments of the invention are disclosed in the dependent claims, the description and the figures.

The orthopedic joint device having an upper part and a lower part which is fastened to the upper part in an articulated manner about a pivot axis, with a flexion-moment-controlled retaining device which is arranged between the upper part and the lower part and which blocks flexion and releases the flexion when a predetermined flexion moment is exceeded, makes provision for the retaining device to be assigned a control element which is coupled to a delay element. With the control element and a combination of the control element with a delay element, it is possible for a smaller flexion moment to have to be applied as the release moment in order to release the retaining device. However, the comparatively smaller moment in relation to conventional joint devices has to be applied over a longer period of time, and therefore, the integral of the moment over time is at least identical, if not even larger than the integral without a delay element. It is thereby possible to bring about a release even if it is not possible to apply a high instantaneous moment that brings about an abrupt release of the retaining device. The flexion lock can thus be removed without the safety during walking or standing being impaired since the locking moment can remain set to a high level. A comparatively small flexion moment has to be applied over a comparatively long period of time before the retaining device is activated to release the flexion, this being carried out, for example, by continuous loading in the flexion direction if there is the desire to sit down. Depending on the configuration of the delay element, the required minimum flexion moment has to be applied over an adapted and adaptable period of time before the retaining device is released. The duration of time for applying the flexion moment can be set and adapted to the respective user of the joint device via the delay element. Automatic unlocking is thus achieved without manual unlocking or by a complicated sensor arrangement. The delay element can be configured in particular as a mechanical and/or hydraulic delay element.

The retaining device can be configured as a mechanical brake or as a pneumatic or hydraulic damper system, or as a pneumatic or hydraulic damper device. The mechanical brake can be configured, for example, as a clamping socket or clamping device which receives an axis of the joint device and reduces the clamping and releases a flexion movement if a sufficiently high flexion moment is exerted for a sufficient duration of time. The clamping device can be an integral part of a joint body, in or on which the upper part and/or the lower part are mounted. It can be configured as a coil-spring brake, shoe brake, or as another mechanical braking device. Alternatively thereto, a fluid-actuated damper device, i.e. a pneumatic or hydraulic damper device, can form the retaining device, in which a flow movement is blocked in order to block the flexion. For this purpose, for example, a valve or another blocking device is provided which is arranged in a fluid line through which the fluid would flow during an unhindered flexion movement. For example, a corresponding control valve or a blocking device which is coupled to a delay element can be arranged in a hydraulic line from a first chamber into a second chamber of a cylinder with a movable piston, or from a first chamber into a reservoir. The control element opens the valve or the other blocking device, preferably slowly, only after a predetermined period of time of application of a flexion moment, in order to avoid an abrupt release and thus a sudden flexion of the joint device under load.

The damper device can have a cylinder in which a movable piston is mounted. The cylinder can be configured both as a rotation cylinder and as a linear cylinder in which the piston executes either a pivoting movement or a linear reciprocal movement along the cylinder wall on a piston rod or a connecting rod. The piston divides the cylinder into at least two chambers such that, when the piston is shifted, and therefore there is an associated reduction in a chamber volume of a first chamber, fluid from the first chamber flows out of the chamber through a line, for example into the at least one further chamber or into a reservoir. Inside the line or the flow path of the fluid, there is a control valve which is in turn assigned the control element in order to set the flow resistance within the line or the flow path, i.e. in order, when a sufficiently high flexion moment is applied for a sufficiently long period of time, which are adjustable, to remove the blocking and thus to reduce the flow resistance from virtually unending.

The control element can be configured as a pneumatic or hydraulic actuator which is connected in terms of flow to at least one chamber of the damper device. The actuator is configured, for example, as a slide, piston or similar pressure-actuated element which, via the pressure applied inside the line because of the applied flexion moment, shifts the control element and thus reduces or changes the flow resistance.

In a development of the invention, it is provided that the control element is designed to be drivable in opposite directions such that, for example, when an extension element is applied, the control element executes a reverse movement, i.e. in particular increases the flow resistance and closes the fluid line, or actuates the mechanical brake, and brings about clamping or some other form of blocking a flexion movement. In the case of a mechanical brake, the blocking can also be realized by a form-fitting device or a form-fitting element which is brought into or out of engagement with a corresponding form-fitting element.

In an embodiment of the retaining device with a damper device, a return line with a check valve can be provided, said return line being coupled to the control element in order to bring about a reciprocal movement of the control element when an extension moment is applied.

The fluid line out of the first chamber can be connected to the other or second chamber or to a compensating volume such that, when the line is released, fluid can flow out of the first chamber and a flexion movement can take place preferably in a controlled manner.

The control element can be configured as a slide, lever or rotary locking mechanism; the control element can likewise have a lever transmission, a gearing or a restoring element in order to be able to undertake a transmission of force and, furthermore, to carry out a reverse movement so that the blocking of the flexion movement is reset or activated after the desired flexion movement or after a certain time.

As shown in FIG. 5, the delay element can be configured as a valve in the fluid line, as a slide mounted in a damped manner, or as a damped motion thread, the delay value of which delay element, and thus the period of time within which a minimum extent of flexion moment has to be applied, can be set.

The control element can be coupled to a force accumulator to counter a reduction in resistance, i.e., for example, can be coupled to a spring or to a compressible fluid which basically loads the control element. It is thereby ensured that a flexion movement is basically blocked and, after the control force with which the control element is brought out of a blocking position into a release position ceases, the blocking position is resumed. The force accumulator which is assigned to the control element is preferably configured to be adjustable in order thereby to be able to set the necessary flexion moment to be applied.

The control element is preferably configured to be actuable under pressure control and with a time delay since control forces to be applied by pressure control can easily be adjusted and can easily be conducted to the respectively required location via corresponding lines. Pressure transmissions by means of piston-cylinder arrangements can also be space-saving. It is also possible for the hydraulic or pneumatic actuation of the control element to be coupled to a mechanical brake. In the case of a retaining device with a damper device, the hydraulic or pneumatic pressure of the damper device can be used at the same time to actuate the control element.

The orthopedic joint device is configured as an orthotic or prosthetic knee joint or orthotic or prosthetic elbow joint or as an orthotic or prosthetic wrist or as a corresponding joint of an exoskeleton as shown in FIG. 4.

A damper device as has been described above can also be advantageously used outside orthopedic joint devices in the field of orthopedic technology, for example for the time-controlled and controlled release of linear movement.

BRIEF DESCRIPTION OF THE DRAWINGS

The invention will be explained in more detail below with reference to exemplary embodiments, in which.

DETAILED DESCRIPTION

Figure 1:
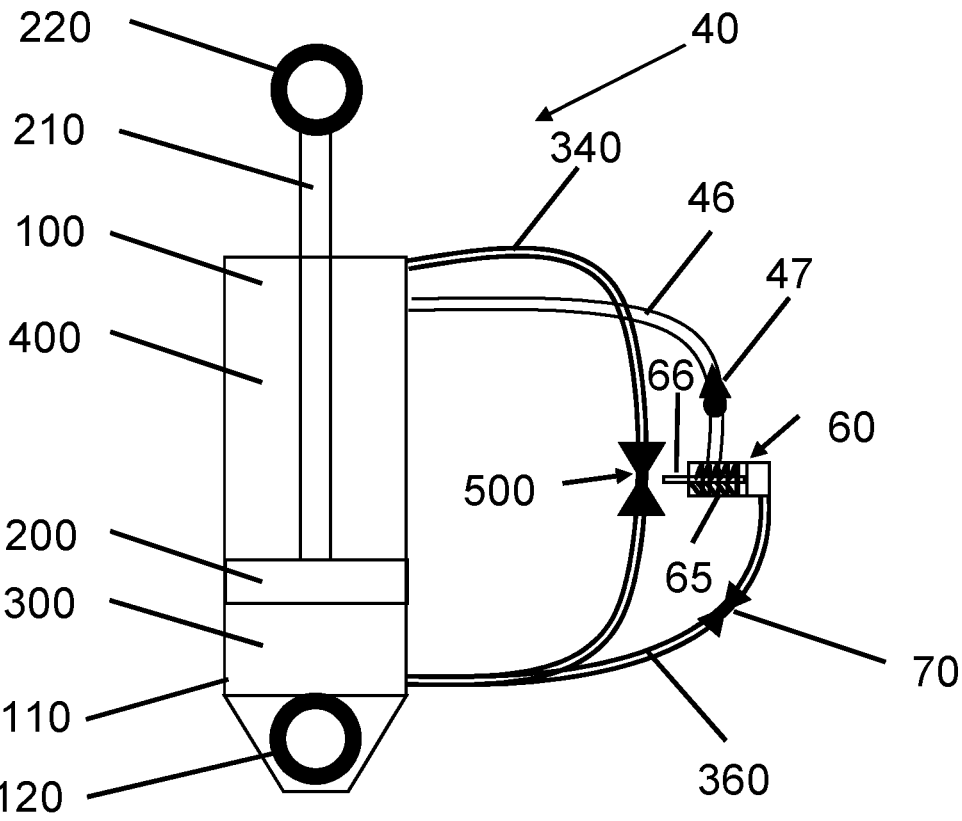
FIG. 1 shows an orthopedic joint device with a damper device.
Figure 3:
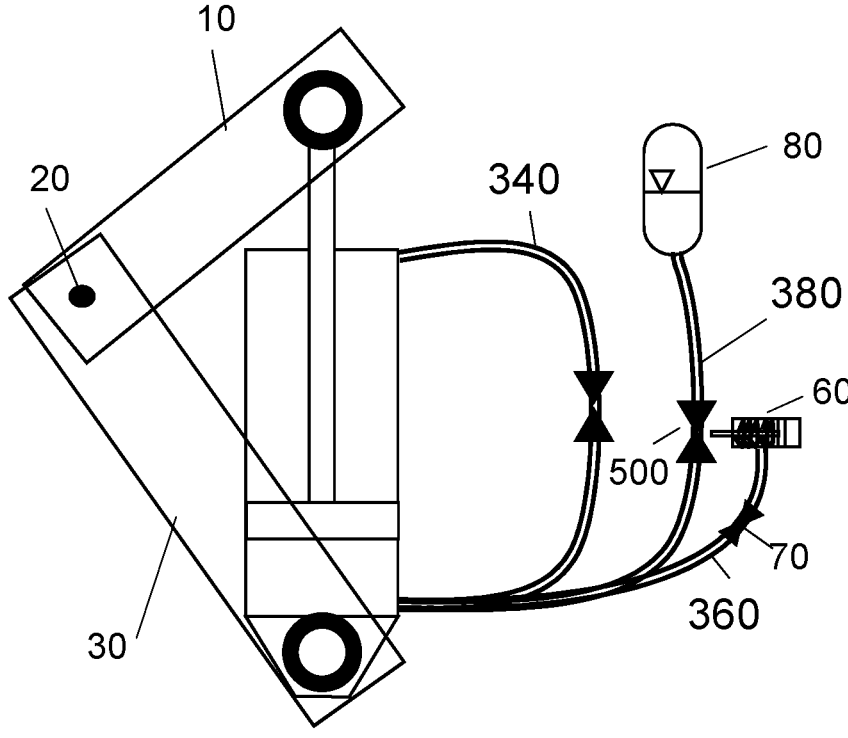
FIG. 3 shows a variant of FIG. 1.
Figure 4:
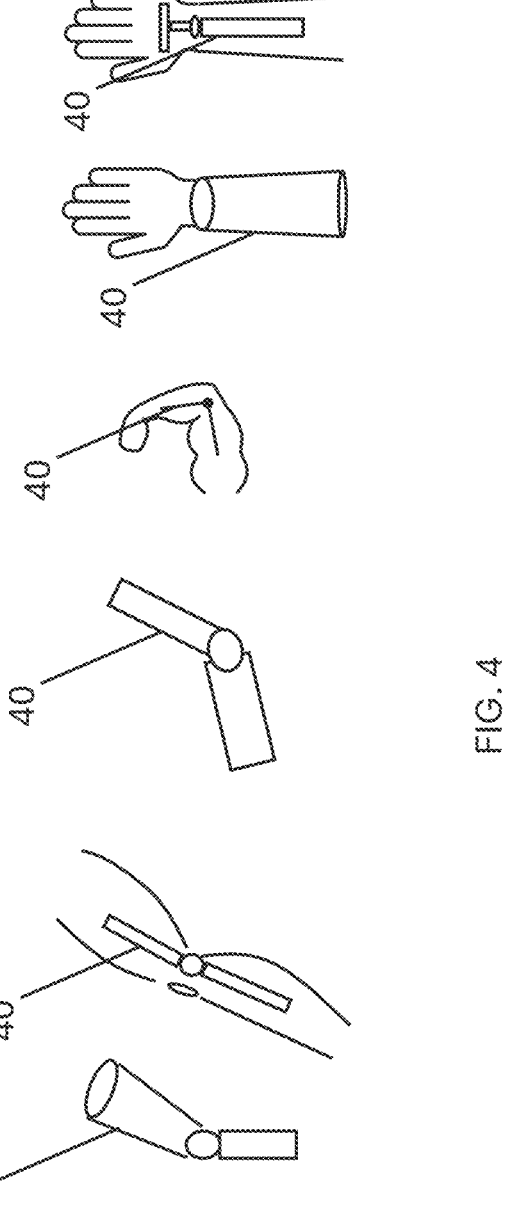
FIG. 4 shows an orthopedic joint device with a mechanical brake.
Figure 5:
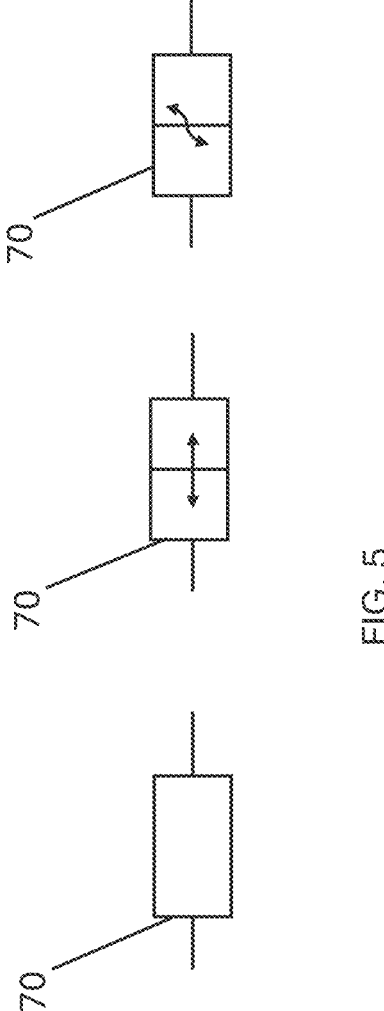
FIG. 5 shows an optional configuration of the delay element and delay value.

FIG. 1, in a schematic illustration, illustrates a retaining device 40 in the form of a hydraulic damper device. The retaining device 40 is arranged between an upper part 10, not illustrated, and a lower part 30 which is fastened in the upper part 10 in an articulated manner about a pivot axis 20. For reasons of clarity, the upper part 10 and the lower part 30 are shown in FIG. 3. The retaining device 40 in the form of a fluidic damper device, in particular a hydraulic damper device, has a cylinder 100 with a cylinder housing 110 in which a piston 200 is mounted in a longitudinally displaceable manner. The piston 200 divides the cylinder 100 into two chambers 300, 400 which are connected to each other in terms of flow via a line 340. The piston 200 is guided on a piston rod 210 which protrudes out of the housing 110. A bearing or axis receptacle 220 is arranged or formed at that end of the piston rod 210 which faces away from the piston 200. A corresponding bearing or axis receptacle 120 is arranged or formed on the housing 110 at that end of the damper device which is opposite the bearing or the axis receptacle 220. A fluid reservoir can be provided in order to compensate for the different changes in volume in the two chambers 300, 400 due to the retracting or extending piston rod 210. If a piston rod is also arranged in the lower first chamber 300, a reservoir can be dispensed with.

In the exemplary embodiment illustrated, the flow line 340 from the first chamber 300 into the second chamber 400 is provided with a control valve 500 which is adjustable in respect of the flow rate and therefore in respect of the flow resistance within the line 340. By changing the flow resistance within the line 340, the resistance against a downward movement or upward movement of the piston 200 and therefore counter to a reduction or increase in volume in one of the two chambers 300, 400 can be set, for example in order to set a flexion resistance or an extension resistance. The resistances can be set differently depending on the direction of movement, for example via a multiway valve with a check valve which, under pressure control or sensor control, block or release a fluid flow in the one or other flow direction.

A control element 60 which is operated under pressure control is assigned to the control valve 500. If the piston 200 is pushed downward by flexion of the joint device, the first chamber 300 is reduced in size, and therefore the fluid, for example hydraulic oil, flows out of the first chamber 300 through the line 340 if the control valve 500 is open. However, the control valve 500 is initially closed and prevents the fluid from flowing through the line 340. A pressure line 360 leading to the control element 60 branches off from the line 340. The control element 60 has a piston in a cylinder with a spring-loaded slide or actuator 66. The piston within the control element 60 pushes against the spring 65 as a force accumulator and shifts the slide 66 toward the control valve 500. If the piston 200 is pressed with a sufficient force, there is a correspondingly high compressive force on the piston within the control element 60, and therefore, depending on the setting of the force accumulator 65 or the pretensioning of the spring, from a certain flexion moment and the associated compressive force on the piston a corresponding shifting of the ram 66 takes place. The ram 66 opens the control valve 500 and reduces the flow resistance in the line 340 such that, after an initial blocking of the flexion movement, the volume from the first chamber 300 can be adjusted into the second chamber 400 such that flexion takes place.

In order to delay the time of the activation of the control element 60 and thus the opening of the line 340 by means of the adjustment of the control valve 500, the pressure line 360 which leads to the control element 60 contains a delay element 70 in the form of a valve or a throttle via which the flow resistance in the line 360 and thus the buildup of pressure in the control element 60 is delayed. The smaller the amount of fluid which can pass from the lower chamber 300 through the delay element 70 into the cylinder of the control element 60 in order to act on the piston arranged there, the longer the flexion moment has to be applied in order to shift the slide 66 until the control valve 500 is opened.

In order to reset the slide 66 or in order to deactivate the control element 60, either the force accumulator 65 is sufficient by itself, the force accumulator pushing the piston back within the control element 60 into the starting position, or a return flow line 46 from the upper chamber 400 is connected via a check valve 47 to a piston chamber of the control element 60 such that a resetting force is exerted during an extension movement because of the hydraulic pressure. An outlet valve or another pressure-reducing device is provided within the control element 60 in order to avoid a hydraulic block-age.

Figure 2:
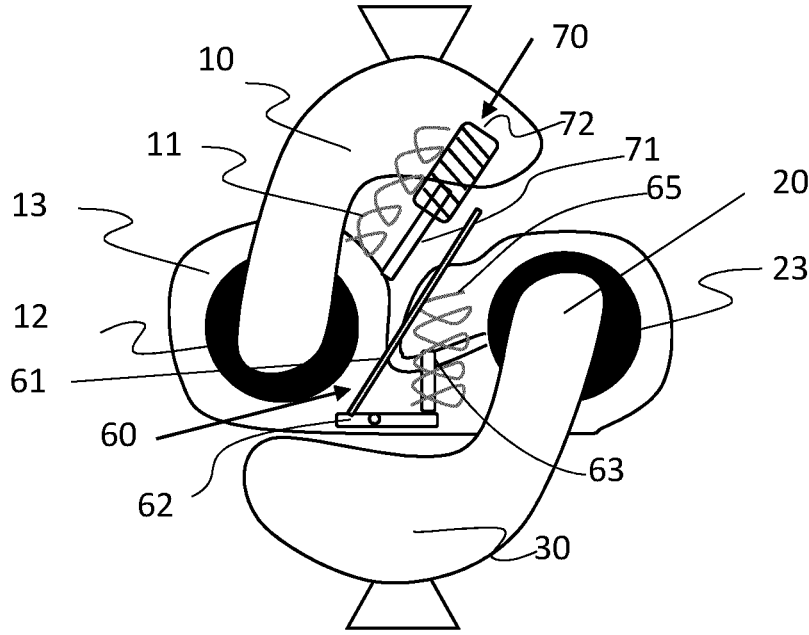
FIG. 2 shows an orthopedic joint device with a mechanical brake.

A variant of the invention is illustrated in FIG. 2 in which the orthopedic joint device is shown as an external knee joint with the upper part 10 and the lower part 30. A joint body 13 in the form of a brake clamp receives the upper part 10 in a pivotable manner. The upper part 10 is mounted pivotably in the joint body 13 with a control axis 12. Analogously thereto, the lower part 30 is mounted pivotably about the pivot axis 20 with a block-able control axis 23. The upper part 10 pivots together with the joint body 13 about the pivot axis 20 if a sufficiently large flexion moment has been applied for a sufficiently long time. The control axis 23 is at the same time a brake axis since the joint body 13 virtually completely circumferentially surrounds the latter, and holds it in a clamping manner, with a gap being left free. If a sufficient flexion moment is applied via the upper part 10 in order to bring about a shifting in the clockwise direction about the control axis 12, the upper part pushes a threaded bushing 72 in the direction of the joint body 13. The bushing 72 is supported on the joint body 13 via a plunger or a rod 71. Also arranged between the joint body 13 and the upper part 10 is a spring 11 or another force accumulator which counteracts a pivoting in the clockwise direction about the control axis 12. The plunger 71 is provided at least with a corresponding thread such that the plunger 71 is screwed into the bushing 72 when the flexion moment is sufficient. Alternatively, the movement of the plunger 71 can be hydraulically damped. The thread within the bushing 72 can be provided with a high-viscosity coating which additionally damps the screwing-in movement, and therefore the plunger 71 is screwed only slowly into the bushing 72. The arrangement of spring 11, bushing 72 and plunger 71 constitutes a delay element 70 which slows down a pivoting in the clockwise direction about the control axis 12. If sufficient pivoting of the upper part 10 is achieved, a bar 61 or a rod 61 is brought into contact with the upper part 10. The rod 61 is arranged on a tilting lever 62 such that, when the upper part 10 is in contact with the rod 61, pivoting about a tilting axis takes place, and therefore the rod end of the tilting lever 62 is shifted downwards. As a result, a second plunger 63 is pivoted upward and pushes against a clamping socket which is part of the joint body 13 and holds the second control axis 320 in a clamping manner by means of a tension spring 65 and prevents a corresponding rotation of the joint body 13 in the clockwise direction about the pivot axis 20. If a sufficiently large force has been applied by means of the second plunger 63 in order to release the brake, when a flexion moment continues to be applied, the upper part 10 pivots in the clockwise direction about the pivot axis 20 relative to the lower part.

When the flexion moment decreases or an extension moment is applied, renewed clamping takes place in order to secure the second control axis 23. In order to permit a resetting movement, a ratchet mechanism can be provided, and therefore an extension movement is always possible. A resetting mechanism or a resetting spring can be formed within the delay element 70 and, when the flexion moment decreases or an extension moment is applied, brings the plunger 71 into its starting position.

FIG. 3 shows a variant of FIG. 1 having a substantially identical design, and therefore not all of the reference signs are shown. A valve or a throttle is arranged in the connecting line 340 between the two chambers 300, 400. The control valve 500, which is coupled to the control element 60 and to the delay element 70, is arranged in a pressure line 380 which leads to a reservoir 80. If the control valve 500 is opened for a sufficient period of time after application of a sufficient flexion moment, fluid flows from the lower chamber through the pressure line 380 into the reservoir 80 and brings about a flexion movement between the upper part 10 and the lower part 30.

the invention claimed is:

1. An orthopedic joint device having an upper part and a lower part which is fastened to the upper part in an articulated manner about a pivot axis, with a flexion-moment-controlled retaining device which is arranged between the upper part and the lower part and which blocks flexion and releases the flexion when a predetermined flexion moment is exceeded, characterized in that the flexion-moment-controlled retaining device is assigned a control element which is coupled to a delay element which causes a time-delay activation of the control element, wherein the control element comprises a pneumatic or hydraulic actuator which is connected in terms of flow to at least one chamber, and wherein the control element comprises a spring-loaded actuator and the delay element comprises a valve or a throttle.

2. The orthopedic joint device according to claim 1, wherein the delay element is configured as a hydraulic delay element.

3. The orthopedic joint device according to claim 1, wherein the flexion-moment-controlled retaining device is configured as a pneumatic or hydraulic damper device.

4. The orthopedic joint device according to claim 3, wherein the pneumatic or hydraulic damper device has a cylinder in which a movable piston is mounted, the movable piston divides the cylinder into two chambers such that, when the movable piston is shifted accompanied by a reduction in a chamber volume, fluid from a first chamber flows out of the first chamber through a line, wherein inside the line there is a control valve which is assigned the control element in order to set a flow resistance.

5. The orthopedic joint device according to claim 1, wherein the control element is configured to be drivable in opposite directions.

6. The orthopedic joint device according to claim 1, wherein a return line with a check valve is coupled to the control element.

7. The orthopedic joint device according to claim 4, wherein the line is connected to a second chamber and/or to a compensating volume.

8. The orthopedic joint device according to claim 1, wherein the valve or the throttle is positioned in a fluid line and comprises a slide.

9. The orthopedic joint device according to claim 1, wherein the delay element is configured to be adjustable.

10. The orthopedic joint device according to claim 1, wherein the control element is coupled to a force accumulator to counter a reduction in resistance.

11. The orthopedic joint device according to claim 10, wherein the force accumulator is configured to be adjustable.

12. The orthopedic joint device according to claim 1, wherein the control element is configured to be actuable under pressure control and with a time delay.

13. The orthopedic joint device according to claim 1, wherein the orthopedic joint device is configured as an orthotic or prosthetic knee joint or as an orthotic or prosthetic elbow joint or as an orthotic or prosthetic wrist.

14. An orthopedic joint device having:

an upper part; and a lower part which is fastened to the upper part in an articulated manner about a pivot axis with a flexion-moment-controlled retaining device which is arranged between the upper part and the lower part, and which blocks flexion and releases the flexion when a predetermined flexion moment is exceeded;

wherein the flexion-moment-controlled retaining device is configured as a pneumatic or hydraulic damper device, and wherein the flexion-moment-controlled retaining device is assigned a control element which is coupled to a delay element, the delay element causes a time-delay activation of the control element, wherein the control element comprises a pneumatic or hydraulic actuator which is connected in terms of flow to at least one chamber, and wherein the control element comprises a spring-loaded actuator and the delay element comprises a valve or a throttle.

15. The orthopedic joint device according to claim 14, wherein the pneumatic or hydraulic damper device has a cylinder in which a movable piston is mounted, the movable piston divides the cylinder into two chambers such that, when the movable piston is shifted accompanied by a reduction in a chamber volume, fluid from a first chamber flows out of the first chamber through a line, wherein inside the line there is a control valve which is assigned the control element in order to set a flow resistance.

16. The orthopedic joint device according to claim 14, wherein the control element is configured to be drivable in opposite directions.

17. An orthopedic joint device having:

an upper part; and a lower part which is fastened to the upper part in an articulated manner about a pivot axis with a flexion-moment-controlled retaining device which is arranged between the upper part and the lower part, and which blocks flexion and releases the flexion when a predetermined flexion moment is exceeded;

wherein the flexion-moment-controlled retaining device is configured as a pneumatic or hydraulic damper device, and wherein the flexion-moment-controlled retaining device is assigned a control element configured as a pneumatic or hydraulic actuator which is connected in terms of flow to at least one chamber, the control element being coupled to a delay element, the delay element causes a time-delay activation of the control element, wherein the control element comprises a pneumatic or hydraulic actuator which is connected in terms of flow to at least one chamber, and wherein the control element comprises a spring-loaded actuator and the delay element comprises a valve or a throttle.

18. An orthopedic joint device having an upper part and a lower part which is fastened to the upper part in an articulated manner about a pivot axis, with a flexion-moment-controlled retaining device which is arranged between the upper part and the lower part and which blocks flexion and releases the flexion when a predetermined flexion moment is exceeded, characterized in that the flexion-moment-controlled retaining device is assigned a control element which is coupled to a delay element which causes a time-delay activation of the control element, wherein fluid from a first chamber flows out of the first chamber through a pressure line to the control element and the delay element is arranged in the pressure line, wherein fluid from the control element flows out of the control element through a return flow line, and wherein a check valve is positioned in the return flow line that prevents flow from a second chamber from entering the control element, and wherein the control element comprises a spring-loaded actuator and the delay element comprises a valve or a throttle.

19. The orthopedic joint device according to claim 18, wherein fluid from the control element flows out of the control element through the return flow line to the second chamber.

20. An orthopedic joint device having an upper part and a lower part which is fastened to the upper part in an articulated manner about a pivot axis, with a flexion-moment-controlled retaining device which is arranged between the upper part and the lower part and which blocks flexion and releases the flexion when a predetermined flexion moment is exceeded, characterized in that the flexion-moment-controlled retaining device is assigned a control element which is coupled to a delay element which causes a time-delay activation of the control element, wherein the control element comprises a pneumatic or hydraulic actuator which is connected in terms of flow to at least one chamber, wherein the control element comprises a spring-loaded actuator and the delay element comprises a valve or a throttle, wherein fluid from a first chamber flows out of the first chamber through a pressure line to the control element and the delay element is arranged in the pressure line, wherein fluid from the control element flows out of the control element through a return flow line, and wherein a check valve is positioned in the return flow line that prevents flow from a second chamber from entering the control element.

21. The orthopedic joint device according to claim 20, wherein fluid from the control element flows out of the control element through the return flow line to the second chamber.

* * * * *